United States Patent
Msika et al.

(10) Patent No.: US 9,439,938 B2
(45) Date of Patent: Sep. 13, 2016

(54) USE OF AVOCADO SKIN FOR OBTAINING AN AVOCADO UNSAPONIFIABLE MATERIAL ENRICHED WITH SATURATED ALIPHATIC HYDROCARBONS AND WITH STEROLS

(71) Applicant: LABORATOIRES EXPANSCIENCE, Courbevoie (FR)

(72) Inventors: Philippe Msika, Versailles (FR); Jacques Legrand, Neuilly sur Eure (FR); Sebastien Garnier, Pierres (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 0 days.

(21) Appl. No.: 14/370,892

(22) PCT Filed: Jan. 14, 2013

(86) PCT No.: PCT/EP2013/050580
§ 371 (c)(1),
(2) Date: Jul. 10, 2014

(87) PCT Pub. No.: WO2013/104793
PCT Pub. Date: Jul. 18, 2013

(65) Prior Publication Data
US 2015/0005273 A1    Jan. 1, 2015

(30) Foreign Application Priority Data

Jan. 13, 2012 (FR) .................................... 12 50367

(51) Int. Cl.
| | |
|---|---|
| A61K 36/54 | (2006.01) |
| A23L 1/30 | (2006.01) |
| A23D 9/00 | (2006.01) |
| A23D 9/02 | (2006.01) |
| C11B 1/08 | (2006.01) |
| A61K 31/01 | (2006.01) |
| A61K 31/575 | (2006.01) |

(52) U.S. Cl.
CPC .................. *A61K 36/54* (2013.01); *A23D 9/00* (2013.01); *A23D 9/02* (2013.01); *A23L 1/3002* (2013.01); *A23L 1/3004* (2013.01); *A23L 1/3006* (2013.01); *A61K 31/01* (2013.01); *A61K 31/575* (2013.01); *C11B 1/08* (2013.01)

(58) Field of Classification Search
CPC ...................................................... A61K 36/54
See application file for complete search history.

(56) References Cited

U.S. PATENT DOCUMENTS

| | | | |
|---|---|---|---|
| 6,582,688 B1 | 6/2003 | Broutin et al. | |
| 6,994,875 B2 | 2/2006 | Piccirilli et al. | |
| 7,863,472 B2 * | 1/2011 | Msika ...................... | A23D 9/00 554/15 |
| 2011/0250154 A1 | 10/2011 | Meretzki et al. | |

FOREIGN PATENT DOCUMENTS

| | | |
|---|---|---|
| FR | 2798667 A1 | 3/2001 |
| WO | 2004012496 A2 | 2/2004 |
| WO | 2010026595 A2 | 3/2010 |

OTHER PUBLICATIONS

Mental Masala, 2010. http://marcsala.blogspot.com/2010/10/does-edible-percentage-of-avocado.html.*
Christiansen BA, Bhatti S, Goudarzi R, Emami S. Management of Osteoarthritis with Avocado/Soybean Unsaponifiables. Cartilage. Jan. 2015;6(1):30-44.*
Kut-Lasserre C, Miller CC, Ejeil AL, Gogly B, Dridi M, Piccardi N, Guillou B, Pellat B, Godeau G. Effect of avocado and soybean unsaponifiables on gelatinase A (MMP-2), stromelysin 1 (MMP-3), and tissue inhibitors of matrix metalloproteinase (TIMP-1 and TIMP-2) secretion by human fibroblasts in culture. J Periodontol. Dec. 2001;72(12):1685-94.*
International Search Report issued in PCT/EP2013/050580.
Anonymous: "ASU Expanscience—Cutting Edge Technology to produce a unique and original ASU." (Feb. 13, 2010) XP002674953.
Werman et al., "Avocado oil production and chemical characteristics," Journal of the American Oil Chemists' Society, 64:2 (Feb. 1, 1987), XP055025527.
Brockisch, "Nahrungsfette and Öle," (Jan. 1, 1993), XP009158090, pp. 73,82,175-177.
Kashman et al., "New Compounds from avacado pear," Tetrahedron, Elsevier Science Publishers, Amsterdam, 25:18 (Jan. 1, 1969), XP002090295.
Brown, "Isolation of unpleasant flavor compounds in the avocado," Journal of Agricultural and Food Chemistry, 20:04 (Jul. 1, 1972), XP055025721.

(Continued)

*Primary Examiner* — Paul Zarek
(74) *Attorney, Agent, or Firm* — Birch, Stewart, Kolasch & Birch, LLP

(57) ABSTRACT

The present invention relates to the use of avocado peels in order to obtain avocado unsaponifiable enriched in saturated aliphatic hydrocarbons and in sterols, said avocado peels accounting for 5 to 50% by weight relative to the total weight of avocado used. The invention also relates to a method for obtaining avocado unsaponifiable enriched in saturated aliphatic hydrocarbons and in sterols from at least avocado peels, said avocado peels accounting for 5 to 50% by weight relative to the total weight of avocado used. The invention also relates to an avocado unsaponifiable enriched in saturated aliphatic hydrocarbons and in sterols, obtainable by this method. Lastly, the invention relates to an avocado unsaponifiable enriched in saturated aliphatic hydrocarbons and in sterols, for use as a drug, advantageously in the in the prevention and/or treatment of conjunctive tissue disorders such as arthrosis, articular pathologies such as rheumatism, or periodontal diseases such as gingivitis or periodontitis.

10 Claims, No Drawings

(56) References Cited

OTHER PUBLICATIONS

Gutfinger et al., "Studies of unsaponifiables in several vegetables oils," Lipids, Springer, 09:09 (Jan. 1, 1974), XP00915877.
Lee et al., "Heptadecanols from the leaves of Persea americana var. americana," Food Chemistry, 132:02 (Nov. 19, 2011) XP055025945.
Mostert, "Characterization of micro-components of avocado oil extracted with supercritical carbon dioxide and their effects on its stability," Extracted from the Internet (Apr. 15, 2008), XP002675113.
Bizimana, "Extraction, characterization, and prediction of the oxidative stability of avocado oil," Dissertation (1997), XP009158924.

* cited by examiner

USE OF AVOCADO SKIN FOR OBTAINING AN AVOCADO UNSAPONIFIABLE MATERIAL ENRICHED WITH SATURATED ALIPHATIC HYDROCARBONS AND WITH STEROLS

CROSS REFERENCE TO RELATED APPLICATIONS

This application is a §371 National Stage Application of PCT/EP2013/050580, filed Jan. 14, 2013, which claims priority to FR 1250367, filed Jan. 13, 2012.

BACKGROUND

1. Field of the Invention

The present invention relates to the use of avocado peels in order to obtain avocado unsaponifiable enriched in saturated aliphatic hydrocarbons and in sterols. Advantageously, said avocado peels account for 5 to 50% by weight relative to the total weight of avocado used. The invention also relates to a method for obtaining avocado unsaponifiable enriched in saturated aliphatic hydrocarbons and in sterols from at least avocado peels, said avocado peels accounting for 5 to 50% by weight relative to the total weight of avocado used. The invention also relates to an avocado unsaponifiable enriched in saturated aliphatic hydrocarbons and in sterols, obtainable by this method. Lastly, the invention relates to one such avocado unsaponifiable enriched in saturated aliphatic hydrocarbons and in sterols, for use as a drug, advantageously in the prevention and/or treatment of conjunctive tissue disorders such as arthrosis, articular pathologies such as rheumatism, or periodontal diseases such as gingivitis or periodontitis.

2. Description of Related Art

Since the 1990s, the worldwide market for the avocado has become diversified. The principal channels remain directed mainly towards export or local markets, depending on the producer country. However, the volumes destined for industry are growing rapidly and are generally related to the processing of fresh pulp into edible products, as well as the production of avocado oil of edible or cosmetic quality.

These latter applications, although they may remain marginal relative to the tonnages dedicated to the marketing of the avocado as a fresh market fruit, make it possible to make use of fruits discarded from the sorting process and fruits rejected by this market. These represent a raw material with a much more acceptable entry cost.

These processing industries are chiefly devoted to adding value to avocado pulp. As a result they generate by-products, resulting from the pulp removal process. For example, the industries that produce guacamole and edible and cosmetic avocado oil, obtained by centrifugation, use only avocado pulp. Thus, very large quantities of co-products, namely the avocado fruits' seeds and peels, are generated which are not made profitable use of by the food processing industry.

Avocado oil is indeed concentrated mainly in the storage cells of the pulp, i.e., the idioblasts. The avocado peel is low in oil and thus holds only little interest for oil producers.

Furthermore, in the traditional avocado oil extraction processes, it is generally sought to remove the avocado peels to the maximum extent possible. To this end, the fruits are thus peeled before oil extraction, because avocado peel contains a high concentration of chlorophylls and pigments which color and darken the oil finally obtained. They can also impact the oxidative and chemical stability of the oil, as well as its suitability for refining.

Markets have been studied and developed to try to develop these by-products, namely the peels and the seeds, such as spreading, mulching, horticulture and animal feeds, but they do not provide high added-value.

However, even if the constituent parts of the avocado, namely the peels and the seeds, are naturally low in oil, they contain compounds constituent of the unsaponifiable with a potential as active ingredients and with high added value.

Nevertheless, as these compounds are in small quantities in these parts of the fruit, such as the peels, they are as a result difficult to reach and to extract.

The high water content of avocados makes them difficult to work with and makes it nearly impossible to process them by the physical extraction methods known to those skilled in the art and under acceptable economic conditions.

Furthermore, the low content of oil and of active compounds in avocado peels precludes the application of a physical treatment by mechanical pressure, this technique being insufficiently effective to process products with oil contents lower than 10%.

Only solvent extraction thus appears possible, although beyond the fact that this method requires a complex technology, it is well-known to be expensive, polluting and toxic for man and the environment.

There thus existed a need to find a method that makes it possible, at low cost, to add value to these active compounds potentially available in easily accessible co-products.

In the past few decades, knowledge of the chemistry of the avocado has expanded considerably. Several families of compounds, for example, have been isolated and identified from the fruits and many studies have been carried out to demonstrate their biological activities. The composition of the unsaponifiable fraction of avocado oil was studied in particular.

The co-products of the avocado processing industry, and notably the peels, are low in oil, but contain all or some of the constituent compounds of the unsaponifiable, in particular compounds of the aliphatic hydrocarbons type with typically an odd number of carbon atoms, of molecular weight near 400 g/mol, and known for their protective and texturing properties.

Furthermore, plant sterols and phytosterols are also constituents of the avocado unsaponifiable and are recognized for, among other things, their anticholesteremic properties, making it possible to limit cardiovascular risks, and for their anti-inflammatory properties.

There has thus been interest in finding a method that makes it possible to extract at lower cost some constituent compounds of avocado unsaponifiable, as mentioned above, in particular from co-products or by-products of the avocado processing industry, such as avocado peels.

The present invention fills this need. The Applicant has thus discovered a novel method for obtaining avocado unsaponifiable enriched in saturated aliphatic hydrocarbons and in sterols, notably from avocado peels.

SUMMARY

The method according to the present invention thus makes it possible to add value to avocado by-products, such as peels, and advantageously to extract the compounds present in the peels that are not extractable by traditional extraction methods. Such compounds are solubilized and then extracted by oil during extraction in the context of the method of the present invention, and value is added as a result.

Furthermore, the increase in the proportion of peels enables, by its mechanical properties, an exchange between the various fractions in contact in the starting material and the extraction of active compounds, which results as a consequence in a notable enrichment of the oil in specific unsaponifiable compounds, such as sterols and saturated aliphatic hydrocarbons.

In an advantageous manner according to the present invention, the oil extracted mainly from the pulp plays a role as a carrier to solubilize and extract the specific unsaponifiable compounds contained in the peels. Due to their lipophilic character, these difficult to reach compounds within the granular structure of the peel are entrained during the pressure extraction step by the flow of oil produced, which diffuses throughout the mass loaded in the extraction press.

In an even more advantageous manner according to the invention, the favorable role of temperature on the extraction rate of these derivatives during oil extraction by mechanical pressure has been demonstrated. Sterols and saturated aliphatic hydrocarbons, due to their molecular structure, have a lipophilic character, but a limited solubility in fats, and as a result are difficult to extract. Pressing at high temperature thus makes it possible to reduce the influence of this property and to guarantee a sufficient level of solubility in order to obtain a high extraction rate with the method by mechanical pressure.

In an even more particular manner according to the invention, it has been shown that the increase in the proportion of peels relative to the various parts of the fruit in the starting mixture had to be very advantageously accompanied by an addition of water or water vapor upstream of the pressure to obtain an optimal pressing yield.

Advantageously according to the invention, the combined contribution of peels in the mass to structure the matrix worked in the extraction press, and then of water or water vapor, generates a gas stream and an increase in pressure within the product which promotes the rupturing of cells, the release of oil, its diffusion in the mass and its expulsion from the press.

Moreover, an avocado unsaponifiable can be advantageously extracted, one enriched in saturated aliphatic hydrocarbons and in sterols, which can be incorporated in cosmetic, dermatological or pharmaceutical compositions or medical devices, or in edible compositions, dietary supplements or nutraceuticals, for humans or animals.

It is thus an object of the present invention to use avocado peels in order to obtain avocado unsaponifiable enriched in saturated aliphatic hydrocarbons and in sterols, said avocado peels advantageously accounting for 5 to 50% by weight relative to the total weight of avocado used. In a particularly advantageous manner, the avocado peels account for 10 to 40%, typically 20 to 40%, by weight relative to the total weight of avocado used. In a particularly advantageous manner, the unsaponifiable according to the invention contains at least 0.2% saturated aliphatic hydrocarbons by weight and at least 1% sterols by weight, relative to the total weight of the unsaponifiable.

DETAILED DESCRIPTION OF A PREFERRED EMBODIMENT

In particular, it is an object of the present invention to use avocado peels in order to obtain by mechanical pressure avocado oil enriched in saturated aliphatic hydrocarbons and in sterols, said avocado peels accounting for 5 to 50% or 10 to 50% by weight relative to the total weight of avocado used, said saturated aliphatic hydrocarbons being typically unbranched linear hydrocarbons with an odd number of carbons.

Advantageously, the saturated aliphatic hydrocarbons are $C_{27}$, $C_{29}$ or $C_{31}$ alkanes, and said sterols are advantageously selected from the group comprised of β-sitosterol, campesterol, stigmasterol, Δ5-avenasterol, Δ7-stigmasterol, citrostadienol, and mixtures thereof.

The present invention also has as an object the use of avocado oil contained in avocado pulp in order to extract saturated aliphatic hydrocarbons and sterols, with avocado pulp accounting for at least 50% by weight relative to the total weight of avocado used.

Most varieties of avocado can be used in the context of the present invention to produce oil and then avocado unsaponifiable, with the characteristics sought, insofar as they contain the qualitative and quantitative potential in terms of specific compounds.

In a particularly advantageous manner, the method of the invention is applied to the most widely cultivated varieties representing the near totality of the tonnages exported and marketed worldwide, preferentially the Hass and Fuerte varieties.

In a particular embodiment of the present invention, the avocados used as the starting product are whole avocados, to which peels may be advantageously added. In an advantageous manner, whole avocados to which peels are added are thus used as the starting mixture.

In the context of the present invention, the term "whole avocados" refers to avocados containing the peel, the pulp and the seed distributed in their integrity.

In another particular embodiment of the present invention, the avocados used as the starting product are avocados without seeds, to which peels can be advantageously added. In an advantageous manner, avocados without seeds to which peels are added are thus used as the starting mixture.

In the context of the present invention, the term "avocados without seeds" refers to whole avocados whose seeds have been removed, and which thus contain only the peel and the pulp.

In another particular embodiment of the present invention, the avocados used as the starting product consist of avocado pulp to which peels are added.

According to a particular characteristic of the invention, the avocados used are soft avocados.

Typically, the soft avocados of the invention have a degree of softening equivalent to that of immediate consumption of the avocado, and exclude pretreatment by slicing.

Advantageously according to the present invention, the soft avocados are characterized by the consistency of their pulp measured using a penetrometer and defined by penetration resistance. In a particularly advantageous manner, the soft avocados have a pulp penetration resistance of less than or equal to 3 kg/cm$^2$, typically less than or equal to 2 kg/cm$^2$, for example less than or equal to 1 kg/cm$^2$.

According to another particular characteristic of the invention, the avocados used are not soft avocados. More particularly, according to one embodiment of the invention, the avocados used are hard avocados.

Advantageously according to the present invention, the hard avocados have a pulp penetration resistance greater than 3 kg/cm$^2$.

Typically according to the present invention, penetration force is measured using a penetrometer of the PCE-PTR 200 or FT 327 type, which measures the force in kilograms required to make a calibrated tip penetrate the fruit. Advantageously, the fruit is peeled before being measured in order to eliminate the resistance of the peel (integument) and the variability in the various varieties of avocado tested. The nominal diameters of the narrow and wide sensor tips used for this measurement are 6 mm and 11.3 mm, respectively.

In a particularly advantageous manner according to the invention, the avocados used are ground and then dried at high temperature, typically between 60 and 150° C., advantageously until a residual moisture content less than or equal to 5% is obtained, before the oil is obtained by mechanical pressure.

According to a particular characteristic of the present invention, following the grinding and drying of the avocados, 1 to 5% water or water vapor, relative to the weight of dried avocados, is added before the oil is obtained by mechanical pressure.

It has indeed been discovered that integrating a step comprised of injecting water or water vapor within the dried avocados makes it possible to obtain avocado oil enriched in saturated aliphatic hydrocarbons and in sterols with a high yield.

The present invention thus has for object the use of avocado peels in order to obtain avocado unsaponifiable enriched in saturated aliphatic hydrocarbons and in sterols. The unsaponifiable of a fat includes all of the components of this fat which, after saponification in strongly alkaline medium, are very poorly soluble or insoluble in water, and soluble in organic solvents, such as ethyl ether, aromatic hydrocarbons, chlorinated solvents, etc.

The unsaponifiable is thus composed of all the non-hydrolysable components of the fat, such as those resulting mainly from the saponification of non-glyceridic fatty acid esters (esters of sterols, waxes, esters of tocopherols, etc.).

Four large groups or families of substances are generally present in most plant oil unsaponifiables. The largest group by weight is represented by the group including sterols, pentacyclic triterpene alcohols and 4-methylsterols. The second group is comprised of tocopherols that can integrate tocotrienols. The two other groups are aliphatic alcohols and saturated and unsaturated aliphatic hydrocarbons.

In particular, the avocado unsaponifiable according to the invention contains saturated aliphatic hydrocarbons and sterols, and is advantageously enriched in saturated aliphatic hydrocarbons and in sterols.

In the context of the present invention, the term "enriched in saturated aliphatic hydrocarbons" refers to an unsaponifiable containing at least 0.2% saturated aliphatic hydrocarbons by weight, relative to the total weight of the unsaponifiable.

Advantageously, the unsaponifiable of the invention contains between 0.2 and 10% saturated aliphatic hydrocarbons by weight, more advantageously between 0.3 and 5% by weight, in particular between 0.4 and 2% by weight, relative to the total weight of the unsaponifiable.

In the context of the invention, the saturated aliphatic hydrocarbons are in particular unbranched, linear hydrocarbons with an odd number of carbons. Advantageously, the saturated aliphatic hydrocarbons are $C_{27}$, $C_{29}$ or $C_{31}$ alkanes.

Typically, the saturated aliphatic hydrocarbons of the invention are selected from the group comprised of n-heptacosane $(CH_3(CH_2)_{25}CH_3)$, n-nonacosane $(CH_3(CH_2)_{27}CH_3)$, n-hentriacontane $(CH_3(CH_2)_{29}CH_3)$, and mixtures thereof.

In the context of the present invention, the term "unsaponifiable enriched in sterols" refers to an unsaponifiable containing at least 1% sterols by weight, relative to the total weight of the unsaponifiable.

Advantageously, the unsaponifiable of the invention contains between 1 and 20% sterols by weight, more advantageously between 2 and 18% sterols by weight, in particular between 3 and 15% sterols by weight, relative to the total weight of the unsaponifiable.

The sterols are in particular tetracyclic hydrocarbons that include an alcohol functional group in position 3 and a double bond whose intracyclic position is mainly in position 5.

In the context of the invention, the sterols are advantageously selected from the group comprised of β-sitosterol, campesterol, stigmasterol, Δ5-avenasterol, Δ7-stigmasterol, citrostadienol, and mixtures thereof.

In a particular embodiment of the present invention, the unsaponifiable contains at least 0.2% saturated aliphatic hydrocarbons by weight, advantageously between 0.2 and 10% by weight, typically between 0.3 and 5% by weight, relative to the total weight of the unsaponifiable, and contains at least 1% sterols by weight, advantageously between 1 and 20% by weight, typically between 2 and 18% by weight, relative to the total weight of the unsaponifiable.

The composition of the avocado unsaponifiable of the present invention differentiates itself from the composition typically found in plant oils, because it mainly integrates specific components of the avocado. In particular, the majority fraction of the avocado unsaponifiable is represented by the group of aliphatic furans. The second family of molecules comprises polyhydroxylated fatty alcohols. The third family is comprised of sterols including pentacyclic triterpene alcohols and 4-methylsterols. The other families include in particular saturated aliphatic hydrocarbons.

Typically, the oil unsaponifiable of the invention also contains alkyl furans and/or alkyl polyols.

Alkyl furans or aliphatic furans are also called furan lipids or more commonly avocadofurans. They are in particular derivatives of persins containing a furan group, which result in particular from the chemical conversion by dehydration and intramolecular cyclization of persins extracted from avocado. For example, mention may be made of the 2-alkyl furans.

Advantageously, the unsaponifiable of the invention contains between 30 and 70% alkyl furans by weight, relative to the total weight of the unsaponifiable.

The alkyl polyols or polyhydroxylated fatty alcohols are in particular triols of the saturated or polyunsaturated, ethylenic or acetylenic long-chain 1,2,4-trihydroxy type.

Advantageously, the unsaponifiable of the invention contains between 5 and 30% alkyl polyols by weight, relative to the total weight of the unsaponifiable.

The present invention also has for object a method for obtaining avocado unsaponifiable enriched in saturated aliphatic hydrocarbons and in sterols from at least avocado peels, said avocado peels accounting for 5 to 50% by weight relative to the total weight of avocado used, including the following successive steps:

Slicing or grinding avocados containing a peel content of 5 to 50% w/w,

High-temperature drying, advantageously at a temperature between 60 and 150° C., in particular between 80 and 120° C., Oil extraction, Alternatively:
  a. Heat treatment of the extracted oil at a temperature advantageously between 80 and 150° C., and then concentration of the oil as its unsaponifiable fraction, or b. Concentration of the oil as its unsaponifiable fraction, and then heat treatment a temperature advantageously between 80 and 150° C., followed by a step of saponification and extraction of the unsaponifiable, and optionally at least a purification and/or a fractionation.

In particular, the present invention has for object a method for obtaining avocado unsaponifiable enriched in saturated aliphatic hydrocarbons and in sterols from at least avocado peels, said avocado peels accounting for 5 to 50% by weight relative to the total weight of avocado used, including the following successive steps:

(1) Cutting or grinding of avocados, said avocados containing a peel content of 5 to 50% w/w, (2) High-temperature drying, advantageously at a temperature between 60 and 150° C., in particular between 80 and 120° C., until a residual moisture content less than or equal to 5% is obtained, (3) Addition of water to the dried avocados by adding 1 to 5% water or water vapor relative to the weight of dried avocados, and then advantageously homogenization by blending, before introduction into the press, and then (4) Oil extraction by mechanical pressure, advantageously at a temperature between 80 and 100° C., (5) Alternatively:

a. Heat treatment of the extracted oil at a temperature advantageously between 80 and 150° C., and then concentration of the oil as its unsaponifiable fraction, or b. Concentration of the oil as its unsaponifiable fraction, and then heat treatment a temperature advantageously between 80 and 150° C., (6) followed by a step of saponification and extraction of the unsaponifiable, (7) and optionally at least a purification and/or fractionation step.

Advantageously according to the present invention, the unsaponifiable contains at least 0.2% saturated aliphatic hydrocarbons by weight and at least 1% sterols by weight, relative to the total weight of the unsaponifiable.

In a particular embodiment of the method of the present invention, the avocados used as the starting product are whole avocados, to which peels can be advantageously added. In an advantageous manner, whole avocados to which peels have been added are thus used as the starting mixture.

The whole avocados are as defined above.

In another particular embodiment of the method of the present invention, the avocados used as the starting product are avocados without seeds, to which peels can be advantageously added. In an advantageous manner, avocados without seeds to which peels are added are thus used as the starting mixture.

The avocados without seeds are as defined above.

In another particular embodiment of the method of the present invention, the avocados used as the starting product consist of avocado pulp to which peels are added.

Advantageously according to the invention, the avocados used as the starting product have a proportion of peels between 10 and 40%, typically 20 to 40%, relative to the total weight of avocado used.

According to a particular characteristic of the invention, the avocados used are soft avocados. The soft avocados are as defined above.

In this case, the first step of the method of the invention consists in the grinding of soft avocados. This step (1) makes it possible to fractionate effectively the various parts of the soft avocado.

It has indeed been discovered that soft fruits do not lend themselves to the usual cutting or drying operations performed on hard avocados.

Indeed, due to the fruit's constitution in three distinct parts, the peel, the pulp and the seed, its behavior during slicing will be highly variable as a function of its degree of maturity and the firmness of the pulp and the peel. In the first phase following its harvest, the fruit has homogeneity of structure and hardness between the three parts, favorable to its slicing. As soon as the pulp begins to soften, the compartmental hardness of the fruit (pulp, peel, seed) becomes very heterogeneous and prevents any industrial slicing due to the presence of the seed, which remains very hard, and to the loss of consistency of the peel and pulp.

Furthermore, it has been discovered that the drying of soft fruits represents a major obstacle to the implementation of the methods known to those skilled in the art in order to extract avocado oil rich in its unsaponifiable fraction.

The drying of soft fruits, notably whole soft fruits, without preparation does not give satisfactory results because it leads to heterogeneous drying favorable to the appearance of parasitic and heterogeneous reactions, factors that degrade the oil and its unsaponifiable.

The grinding and the drying of soft fruit under less than controlled conditions lead to the same phenomena and to the production of oil of highly variable quality, which limits or penalizes its uses.

In a particular embodiment of the present invention, grinding (1) is carried out on whole avocados made up of the peel, pulp and the seed, or on avocados without seeds made up of the peel and pulp.

Grinding (1) advantageously makes it possible to shred the peel, to break up the seed and to mix the mixture in order to obtain a homogeneous dispersion and particle size distribution of the ground material (particles and pieces obtained) in the avocado pulp.

Typically, the grinding mills used adapt to the very wide difference in texture and hardness of the various parts that compose the avocado, namely the peel, pulp and seed. Thus, the technology of the grinding mills to be used must make it possible to process materials with a very hard part (seed), a softer part (peel) and a very soft part (pulp).

Grinding (1) is advantageously carried out using a grinding mill of the type with blades or notched rollers.

The configuration and settings must be, however, generally adapted as a function of the size, maturity and quality of the fruits (biometry of the seed, pulp and peel) in order to produce the particle size distribution advantageously sought.

In a particularly advantageous manner according to the invention, grinding (1) is carried out so as to obtain a specific size of particles and pieces, with a particle size distribution that gives to the ground material a texture suited to rapid drying. This texture is characterized by a discontinuous visual appearance, as the pieces are generally detectable in the mass without the use of an additional optical instrument. Typically, the surface of the ground material is not smooth and includes asperities represented by the particles of seed and peel. During drying, the ground material does not form a compact mass, but blocks that crumble easily.

Advantageously, grinding (1) produces a particle size distribution of the ground material between 2 and 20 mm, in particular between 2 and 10 mm.

In an advantageous manner according to the invention, the mixture, once ground, must be distributed in a way suited to guarantee homogeneity of the following drying step (2) with the greatest efficiency, advantageously by spreading out in a thin layer, typically to lead to a layer of small thickness advantageously between 0.5 and 5 cm, in particular between 1 and 2 cm, or by shaping, making it possible to optimize the evaporation surface, such as extrusion or molding in a die.

According to another particular characteristic of the invention, the avocados used are hard avocados. The hard avocados are as defined above.

In this case, the first step of the method of the invention consists of the slicing of hard avocados.

The slicing (1) of the avocados is typically carried out using a disc slicer.

The slicing (1) of the avocados leads advantageously to slices 2 to 5 mm in thickness.

The slices are then distributed in a homogeneous manner on drying trays or racks.

The purpose of the following drying step (2) is to extract water from the medium, but also to make the compounds of the unsaponifiable extractable. This is carried out, in particular, thanks to a specific technology and to a temperature selected to optimize energy needs and to limit undesirable reactions. Indeed, a too low temperature limits the water evaporation rate and promotes the action of lipases, leading to glyceride hydrolysis and an increase in the acid value of the medium. A too high temperature promotes the phenomenon of buildup, as well as the thermal and/or oxidative or non-oxidative degradation (Maillard reaction) of the sensitive compounds of the unsaponifiable or the unsaturated compounds of the oil.

It has thus been discovered that it is advisable to use a step of drying at gentle and controlled temperature. The avocado's very high water content (≈75%) thus requires a very efficient and specific drying technique in order to guarantee rapid evaporation that does not induce degradation of the constituents of the fruit.

In a particularly advantageous manner according to the invention, drying (2) is carried out at a gentle and controlled temperature, advantageously at a temperature between 60 and 150° C., in particular between 65 and 120° C., for example between 80 and 120° C. or 70 and 100° C., typically between 80 and 100° C.

According to a particular characteristic of the invention, drying (2) is carried out for 8 to 78 hours, advantageously for 10 to 24 hours.

The drying (2) of the invention can be carried out in particular by drying under a stream of hot air or under controlled atmosphere (e.g., nitrogen), by drying at atmospheric pressure or under vacuum, or by microwave drying.

In the context of the present method, for reasons of ease of industrial implementation and for reasons of cost, drying in ventilated drying chambers, in thin layers and under a stream of hot air, at a temperature between 80 and 100° C., for 8 to 36 hours is preferred.

Advantageously, at the conclusion of the drying step (2), the dried product has a residual water content less than or equal to 5% w/w.

Residual moisture is typically measured using a thermogravimetric method by IR drying. Other methods can also be used, such as the loss on drying method or the Karl Fischer titration method.

A residual moisture content less than or equal to 5% plays an important role in the consistency of dried avocados, conferring on them a favorable brittle solid texture to resist the physical forces built up under mechanical pressure.

Above 5% moisture, the dried avocado has a soft consistency that leads, during pressing, to the formation of a mash without sufficient consistency to be pressed efficiently.

It has been found that, even with a residual moisture content less than or equal to 5% and a consistency suitable to pressing, these conditions are not completely sufficient to achieve the pressure conditions that enable a high yield of extracted oil.

It has thus been discovered in a surprising manner that a readjustment (3) of the residual moisture by adding 1 to 5% water or water vapor, for example from 1 to 3% water or water vapor, relative to the weight of dried avocados, makes it possible to increase considerably the rate of oil extraction, and as a result pressing efficiency.

This operation of readjustment/addition of water (3) must be advantageously carried out just before the introduction of the dried fruits into the press by the addition of purified water or water vapor so that the dried avocados become saturated with moisture without losing their firm consistency and so that no softening occurs.

For this residual water content to be effective it may be obtained only by preliminary dehydration (2) of the avocados, and then readjustment by the addition of water (3). Indeed, direct controlled partial dehydration does not lead to a product texture compatible with pressing, as indicated above.

In a particular manner according to the invention, the addition of water (3) to the dried avocados is carried out by the controlled addition of water or water vapor to the dried avocados, and then homogenization by blending typically in a planetary mixer, advantageously for 30 minutes to 1 hour.

In a more particular manner according to the invention, the addition of water (3) to the dried avocados is carried out continuously in a screw conveyor. The water or water vapor is added to the avocados at the head of the conveyer and homogenization is obtained by mixing in the conveyer, during the movement of the product. The dimensions of the conveyer must make it possible to typically guarantee that the dried avocados are processed for a minimum of 30 minutes.

In an even more particular manner according to the invention, the conveyer is used to feed the extraction press.

The oil extraction step (4) is thus particularly advantageously preceded by a step of the addition of water (3) to the dried avocados by adding 1 to 5% water or water vapor, preferably of 1 to 3%, relative to the weight of dried avocados.

The oil extraction step (4) is advantageously implemented by mechanical pressing of the dry matter, advantageously after implementing the water addition step (3).

Usually, to be able to work efficiently, extraction presses must receive material containing a content of fibers and suitable organic matter conferring a certain consistency on the oil cake produced. This consistency makes it possible to achieve, at the head of the press, a high pressure that is essential in order to guarantee a suitable pressing yield.

Advantageously, the presence of particles of peel within the mixture gives it a consistency and texture favorable to the extraction of the oil by pressure and as a result improves the productivity and the production of the oil by pressure.

Advantageously, the extraction step (4) is carried out at a temperature between 80 and 100° C. This temperature is obtained and maintained constant by all available means, such as preheating the press unit, preheating the dried avocados and then adding water through a supply to the press, heating the press unit, etc.

In particular, maintaining the working temperature of the press at a value greater than 80° C., more particularly 100° C., makes it possible to guarantee a satisfactory level of oil extraction and to notably improve the extraction yield of the constituents of the unsaponifiable, in particular sterols and/or saturated aliphatic hydrocarbons.

The extraction step (4) of the invention is generally supplemented by filtration which eliminates the solid particles and guarantees the clarity of the oil produced.

The step of the concentration of the oil in its unsaponifiable fraction in order to prepare a concentrate, implemented in step (5)a or (5)b, is described in particular below.

The step of concentration of the oil in its unsaponifiable fraction (5)a or (5)b is generally carried out by cold crystallization or molecular distillation. Advantageously, the concentrate of avocado oil unsaponifiable is prepared by molecular distillation, typically at a temperature between 180 and 260° C., while maintaining a pressure between $10^{-2}$ and $10^{-3}$ mmHg.

This step of molecular distillation of the avocado oil is preferably carried out by using a device selected from molecular distillers of the centrifugal type and devices of the wiped film type.

The step of heat treatment of the oil or the concentrate, implemented in step (5)a or (5)b, is generally carried out at a temperature between 80 and 150° C., for example between 80 and 130° C.

The method for preparing avocado unsaponifiable enriched in saturated aliphatic hydrocarbons and in sterols includes a step (6) of saponification and extraction of the unsaponifiable, for example using a solvent.

In particular, the step (6) of the saponification and the extraction of the unsaponifiable can be implemented in the presence of potassium hydroxide or of sodium hydroxide in an alcoholic medium, preferably ethanolic, followed by one or more extractions. The extraction by a suitable organic solvent (liquid-liquid extraction) in order to separate the soap fatty acids and the unsaponifiable compounds is particularly suited. The suitable organic solvent may be, for example, selected from the group of alkanes, halogenated alkanes, aromatic and halogenated aromatic solvents, ethers, ketones, esters, solvents including at least one silicon atom or any other suitable solvent that is immiscible with the hydroalcoholic solution.

Following the extraction of the unsaponifiable, supplemental steps (7) of purification or of fractionation may be undertaken.

The present invention also has for object an avocado unsaponifiable enriched in saturated aliphatic hydrocarbons and in sterols, obtainable by the method according to the invention.

Advantageously, the unsaponifiable of the invention contains at least 0.2% saturated aliphatic hydrocarbons by weight, advantageously between 0.2 and 10% by weight, more advantageously between 0.3 and 5% by weight, in particular between 0.4 and 2% by weight, relative to the total weight of the unsaponifiable.

The saturated aliphatic hydrocarbons are as defined above and are typically unbranched linear hydrocarbons with an odd number of carbons. Advantageously, the saturated aliphatic hydrocarbons are $C_{27}$, $C_{29}$ or $C_{31}$ alkanes, in particular selected from the group comprised of n-heptacosane, n-nonacosane, n-hentriacontane, and mixtures thereof.

Advantageously, the unsaponifiable of the invention contains at least 1% sterols by weight, advantageously between 1 and 20% by weight, more advantageously between 2 and 18% by weight, in particular between 3 and 15% by weight, relative to the total weight of the unsaponifiable.

The sterols are as defined above and are typically selected from the group comprised of β-sitosterol, campesterol, stigmasterol, Δ5-avenasterol, Δ7-stigmasterol, citrostadienol, and mixtures thereof.

In a particular embodiment of the present invention, the unsaponifiable contains at least 0.2% saturated aliphatic hydrocarbons by weight, advantageously between 0.2 and 10% by weight, typically between 0.3 and 5% by weight, relative to the total weight of the unsaponifiable, and contains at least 1% sterols by weight, advantageously between 1 and 20% by weight, typically between 2 and 18% by weight, relative to the total weight of the unsaponifiable.

Typically, the oil unsaponifiable according to the invention also contains alkyl furans and/or alkyl polyols, as defined above.

Advantageously, the unsaponifiable of the invention contains between 30 and 70% alkyl furans by weight, relative to the total weight of the unsaponifiable.

Furthermore, the unsaponifiable of the invention generally contains between 5 and 30% alkyl polyols by weight, relative to the total weight of the unsaponifiable.

The present invention also has for object a composition containing an unsaponifiable of the invention as mentioned above, advantageously at a concentration between 0.1 and 99.9% by weight, even more advantageously from 30 to 70% by weight, relative to the total weight of the composition.

The composition according to the invention may, moreover, include other active ingredients.

Among the active ingredients recommended in combination with the unsaponifiable of the invention, mention may be made of plant extracts, in particular:
- plant oils or butters such as soy oils and/or rapeseed oil, lupin oil, advantageously sweet white lupin oil, or a mixture of these oils or butters;
- the oleodistillate or the concentrates of plant or animal oil, in particular of sunflower, more advantageously linoleic sunflower concentrates, such as sunflower oil concentrated in unsaponifiable (Soline®) marketed by Laboratoires Expanscience, oils concentrated in unsaponifiable of the soy oil, rapeseed oil, corn oil or palm oil type;
- unsaponifiables of plants or plant oil, advantageously of avocado furans (Avocadofurane®), avocado and/or soy unsaponifiables, more particularly a mixture of furanic unsaponifiables of avocado and unsaponifiables of soy, advantageously in a respective ratio of about 1/3-2/3 (such as Piascledine® 300), soy unsaponifiables, sterolic unsaponifiables (typically unsaponifiables whose total content in sterols, methylsterols and triterpene alcohols is between 20 and 95% by weight, preferably 45-65% by weight, relative to the total weight of unsaponifiable), phytosterols, sterol esters and vitamin derivatives.

In particular, the composition of the invention contains an avocado unsaponifiable of the invention, in combination with a soy unsaponifiable, advantageously in a ratio of about 2/3 for soy and 1/3 for avocado (such as Piascledine® 300).

In a particular embodiment of the present invention, the composition further includes at least one compound selected from the following compounds, known for their properties in the treatment of conjunctive tissue, in particular in the treatment of arthrosis: amino sugars such as glucosamine; glucosamine salts, such as glucosamine hydrochloride (1500 to 2000 mg/day, for example), glucosamine sulfate, glucosamine phosphate and N-acetylglucosamine; glycosaminoglycans (GAGs) such as chondroitin sulfate (800 to 1200 mg/day, for example); glycosaminoglycan analogues such as polysulfated glycosaminoglycans, or glycosaminoglycan precursors such as hyaluronic acid, glucuronic acid, iduronic acid, keratan sulfate, heparan sulfate, or dermatan sulfate; pentosan or derivatives thereof, in particular pentosan sulfate, pentosan polysulfate (PPS) and polysaccharide pentosan polysulfates; S-adenosylmethionine (SAMe); adenosine; superoxide dismutase (SOD); L-ergothioneine; type II collagens, hydrolyzed or not; collagen hydrolysates such as gelatin; diacerin; arachidonic acid; tetracycline; tetracycline analog compounds; doxycycline; hydroxyproline; and mixtures thereof.

Advantageously, the composition of the present invention includes in combination several of the compounds mentioned above. Glucosamine and chondroitin sulfate, alone or in combination, are particularly preferred compounds.

In another particular embodiment of the present invention, the composition further includes at least one non-steroidal anti-inflammatory drug (NSAID), such as acetaminophen.

Lastly, the present invention also has for object an avocado unsaponifiable enriched in saturated aliphatic hydrocarbons and in sterols, as described above, or the composition as described above, for use as a drug, medical device, dermatological agent, cosmetic agent or nutraceutical, for humans or animals, advantageously in the prevention and/or treatment of conjunctive tissue disorders such as arthrosis, articular pathologies such as rheumatism, periodontal diseases such as gingivitis or periodontitis, or in the prevention and/or treatment of the disorders of the dermis and/or the hypodermis such as cutaneous aging, stretch marks and cellulitis, or of disorders of the epidermal barrier such as cutaneous inflammation, atopic eczema and irritative and/or inflammatory dermatitis.

In particular, the present invention has for object an avocado unsaponifiable enriched in saturated aliphatic hydrocarbons and in sterols, obtained by the method of the invention, for use as a drug, advantageously in the prevention and/or treatment of conjunctive tissue disorders such as arthrosis, articular pathologies such as rheumatism, or periodontal diseases such as gingivitis or periodontitis.

Furthermore, in the context of the present invention, the term "medical device" refers to any instrument, apparatus, equipment, material, product, except for products of human origin, or another item alone or in combination, intended by the manufacturer to be used in humans for medical purposes and whose desired principal action is not obtained by pharmacological or immunological means or by metabolism, but whose function can be assisted by such means.

Advantageously, the compositions of the invention are suited to oral administration, such as a pharmaceutical composition or a drug, an edible supplement or a nutraceutical composition.

According to one variant, the compositions of the invention are suited to topical application and notably include creams, emulsions, milks, pomades, lotions, oils, aqueous or hydroalcoholic or glycolic solutions, powders, patches, sprays, shampoos, varnishes or any other product for external application.

The following examples are given to illustrate the invention:

EXAMPLE 1

Contribution of the Addition of Water to Dried Avocados Before Pressing and of Pressing Temperature 3 kg of Kenyan avocados, caliber 18, Hass variety, with hardness measured using a penetrometer greater than 13 kg/cm$^2$ and with 14.3% peel by weight, are ground in a Retsch knife grinder of the SM 100 type equipped according to the particle size distribution desired with a bottom sieve with an aperture size of 10 mm.

The ground material is deposited on a 0.158 m$^2$ tray to a depth of 2 cm.

The tray is then placed in a ventilated oven and drying is carried out under circulating air at a temperature of 80±5° C. for 24 hours.

The dried ground material is recovered and ground for homogenization on a Retsch knife grinder of the SM 100 type equipped with a bottom sieve with an aperture size of 20 mm.

According to the tests, water is then added or not added to the ground material by vaporization of a suitable quantity of purified water and the mixture is homogenized in a planetary mixer just before being introduced into the press for extraction of the oil.

The avocado oil is then extracted by mechanical pressure on a laboratory screw press of the Komet type preheated at the temperature determined by the test.

The quantities of oil and oil cake are determined by weighing for each test and the extraction yield is calculated by the following formula:

Weight of oil recovered×100/(Weight of oil recovered+Weight of oil cake).

Avocado oils from the various tests are filtered, and then distilled on a wiped-film molecular distiller of the Leybold KDL 4 type at a temperature of 230° C. and under a vacuum of $10^{-2}$ to $10^{-3}$ mmHg.

The distillates concentrated in unsaponifiable are heated at 85° C. for 48 hours under a stream of nitrogen in a stirred reactor.

The distillates are then solubilized in ethanol and saponified with 50% potassium hydroxide and by heating the alcohol under reflux for 4 hours.

The reaction mixtures are then diluted with purified water, and then extracted with 1,2-dichloroethane in a separating funnel. The extraction is continued with repeated volumes of solvent until colorless lower organic phases are obtained.

The organic phases are combined, washed with water to obtain neutral pH, dried on anhydrous sodium sulfate and then evaporated under vacuum in a rotary evaporator to remove the solvent and to recover the unsaponifiable. The recovered products are then packaged under nitrogen and are analyzed.

The chromatographic analyses of the unsaponifiables obtained provided the following results (% by weight):

|      |                                    |                               | Oil                            |                              |                              |                              | Composition of the unsaponifiable |
|------|------------------------------------|-------------------------------|--------------------------------|------------------------------|------------------------------|------------------------------|-----------------------------------|
| Test | Water added after drying % | Pressing temperature ° C. | extraction yield % | Distillation rate % | Unsaponifiable yield % | Sterol content w/w | Saturated aliphatic hydrocarbons content w/w |
| 1    | 0                                  | 80                            | 15.2                           | 11.09                        | 58.4                         | 7.63                         | 0.40                              |
| 2    | 3                                  | 80                            | 40.0                           | 11.40                        | 58.3                         | 7.90                         | 0.42                              |
| 3    | 3                                  | 100                           | 40.4                           | 12.40                        | 59.9                         | 8.40                         | 0.58                              |

Tests 1 and 2 demonstrate that the addition of water to the dried fruits before pressing makes it possible to achieve a high pressing yield in the case of test 2, contrary to test 1 in which no water addition step was performed.

Tests 2 and 3, compared to test 1, demonstrate the cumulative benefit of the temperature and the addition of water to the dried avocados on the pressing yield and on the composition of the unsaponifiable, notably on its content of sterols and saturated aliphatic hydrocarbons.

COMPARATIVE EXAMPLE 2

Pulp Alone 100 kg of fresh pulp, mashed, is spread on trays in a thin layer to a depth of a few millimeters and drying takes place in a ventilated oven at a temperature of 80° C. for 24 hours. The dried product is then ground in a hammer mill.

29.5 kg of dry pulp is recovered, which represents a loss on drying of 70.5%.

Oil is extracted by mechanical pressure on a Komet-type laboratory press after the addition of 2% water on the dried pulp and homogenization for 30 minutes in a planetary mixer. The oil is then filtered on a bell-shaped filter under nitrogen pressure and packaged under nitrogen atmosphere.

The filtered oil is then distilled on a wiped-film molecular distiller of the Leybold KDL 4 type at a temperature of 230° C. and under a vacuum of $10^{-2}$ to $10^{-3}$ mmHg. The distillation rate obtained for this operation is 10.8%.

In the following step, the distillate concentrated in unsaponifiable is heated at 85° C. for 48 hours under a stream of nitrogen in a stirred reactor.

The distillate in solution in ethanol is then saponified by 50% potassium hydroxide and by heating the alcohol under reflux for 4 hours.

The reaction mixture is then diluted with purified water and then extracted with 1,2-dichloroethane in a separating funnel. The extraction is continued with repeated volumes of solvent until a colorless lower organic phase is obtained.

The organic phases are combined, washed with water to obtain neutral pH, dried on anhydrous sodium sulfate and then evaporated under vacuum in a rotary evaporator to remove the solvent and to recover the unsaponifiable. The recovered product is then packaged under nitrogen and analyzed.

The chromatographic analyses of the unsaponifiable obtained provided the following results (% by weight):
Proportion of alkyl furans: 67.9%;
Proportion of alkyl polyols: 23.5%;
Proportion of sterols: 8.5%;
Proportion of saturated aliphatic hydrocarbons: 0.1%.

The protocol described in example 2 was then reproduced in the following examples, presented below. The percentages are expressed by weight.

EXAMPLE 3

Mixture of Pulp with 20% Peels 80 kg of moist pulp is ground with 20 kg of moist peels and then spread on trays in a thin layer to a depth of a few millimeters.

28.8 kg of dry pulp+peels is recovered representing a loss on drying of 71.2%.

The chromatographic analyses of the final unsaponifiable obtained provided the following results:
Proportion of alkyl furans: 67.2%;
Proportion of alkyl polyols: 23.2%;
Proportion of sterols: 9.1%;
Proportion of saturated aliphatic hydrocarbons: 0.5%.

Thus, the use of 20% peels in the avocado mixture used makes it possible to multiply by 5 the proportion of saturated aliphatic hydrocarbons and to increase by 7% the proportion of sterols in the unsaponifiable prepared relative to a product prepared from pulp alone (example 2).

EXAMPLE 4

Mixture of Pulp with 40% Peels 60 kg of moist pulp is ground with 40 kg of moist peels and then spread on trays in a thin layer to a depth of a few millimeters.

28.1 kg of dry pulp+peels is recovered representing a loss on drying of 71.9%.

The chromatographic analyses of the final unsaponifiable obtained provided the following results:
Proportion of alkyl furans: 65.9%;
Proportion of alkyl polyols: 22.8%;
Proportion of sterols: 9.8%;
Proportion of saturated aliphatic hydrocarbons: 1.5%.

Thus, the use of 40% peels in the avocado mixture used makes it possible to multiply by 15 the proportion of saturated aliphatic hydrocarbons and to increase by 15% the proportion of sterols in the unsaponifiable prepared relative to a product prepared from pulp alone (example 2).

EXAMPLE 5

Whole Hard Fruits Including 15% Peels

The average penetration resistance of the avocados is greater than 13 kg/cm².

100 kg of fresh whole fruits is cut into 2 to 5 mm slices, and then divided into regular layers on plates.

31.2 kg of dried avocados is recovered representing a loss on drying of 68.8%.

The chromatographic analyses of the final unsaponifiable obtained provided the following results:

Proportion of alkyl furans: 67.0%;
Proportion of alkyl polyols: 23.6%;
Proportion of sterols: 8.8%;
Proportion of saturated aliphatic hydrocarbons: 0.58%.

Thus, the use of 15% peels in the avocado mixture used makes it possible to multiply by 5.8 the proportion of saturated aliphatic hydrocarbons and to increase by 3.5% the proportion of sterols in the unsaponifiable prepared relative to a product prepared from pulp alone (example 2).

EXAMPLE 6

Whole Hard Fruits to which Peels are Added (32% Peels)

The peels are present here in a proportion of 32% by weight in the starting mixture used (whole hard fruits+peels).

The average penetration resistance of the avocados is greater than 13 kg/cm$^2$.

80 kg of fresh whole hard fruits to which 20 kg of moist peels is added is cut into 2 to 5 mm slices and then distributed in even layers on trays.

37.7 kg of dried avocados+peels is recovered representing a loss on drying of 62.3%.

The chromatographic analyses of the final unsaponifiable obtained provided the following results:

Proportion of alkyl furans: 66.0%;
Proportion of alkyl polyols: 23.2%;
Proportion of sterols: 9.6%;
Proportion of saturated aliphatic hydrocarbons: 1.18%.

Thus, the use of 32% peels in the avocado mixture used makes it possible to multiply by 11.8 the proportion of saturated aliphatic hydrocarbons and to increase by 13% the proportion of sterols in the unsaponifiable prepared relative to a product prepared from pulp alone (example 2).

EXAMPLE 7

Whole Hard Fruits to which Peels are Added (49% Peels)

The peels are present here in a proportion of 49% by weight in the starting mixture used (whole hard fruits+peels).

The average penetration resistance of the avocados is greater than 13 kg/cm$^2$.

60 kg of fresh whole fruits to which 40 kg of moist peels is added is cut into 2 to 5 mm slices and then distributed in even layers on trays.

44.2 kg of dried avocados+peels is recovered representing a loss on drying of 55.8%.

The chromatographic analyses of the final unsaponifiable obtained provided the following results:

Proportion of alkyl furans: 65.1%;
Proportion of alkyl polyols: 23.0%;
Proportion of sterols: 10.1%;
Proportion of saturated aliphatic hydrocarbons: 1.79%.

Thus, the use of 49% peels in the avocado mixture used makes it possible to multiply by 17.9 the proportion of saturated aliphatic hydrocarbons and to increase by 18.8% the proportion of sterols in the unsaponifiable prepared relative to a product prepared from pulp alone (example 2).

EXAMPLE 8

Whole Soft Fruits Including Peels (15%)

The average penetration resistance of the avocados is less than 2 kg/cm$^2$.

100 kg of soft whole avocados is ground in a cutting mull and then spread on trays in a thin layer to a depth of a few millimeters.

35.2 kg of dried avocados is recovered representing a loss on drying of 64.8%.

The chromatographic analyses of the final unsaponifiable obtained provided the following results:

Proportion of alkyl furans: 62.4%;
Proportion of alkyl polyols: 24.9%;
Proportion of sterols: 9.2%;
Proportion of saturated aliphatic hydrocarbons: 0.52%.

Thus, the use of 15% peels in the soft avocado mixture used makes it possible to multiply by 5.2 the proportion of saturated aliphatic hydrocarbons and to increase by 8.2% the proportion of sterols in the unsaponifiable prepared relative to a product prepared from pulp alone (example 2).

The table below summarizes the results of the various tests 2 to 8:

| Test | Material extracted from the avocado | Proportion of sterols % w/w | Increase in sterols relative to pulp alone % | Proportion of saturated aliphatic hydrocarbons % w/w | Hydrocarbon increase relative to pulp alone % |
|---|---|---|---|---|---|
| 2 | Pulp | 8.5 | — | 0.10 | — |
| 3 | 80% pulp 20% peels | 9.1 | 7 | 0.50 | 500 |
| 4 | 60% pulp 40% peels | 9.8 | 15 | 1.50 | 1500 |
| 5 | Whole hard avocados including 15% peels | 8.8 | 3.5 | 0.58 | 580 |
| 6 | Whole hard avocados including 32% peels | 9.6 | 13 | 1.18 | 1180 |
| 7 | Whole hard avocados including 49% peels | 10.1 | 18.8 | 1.79 | 1790 |
| 8 | Whole soft avocados including 15% peels | 9.2 | 8.2 | 0.52 | 520 |

The invention claimed is:

1. A process for obtaining avocado unsaponifiable enriched in saturated aliphatic hydrocarbons and in sterols from at least avocado peels, said avocado peels accounting for 5 to 50% by weight relative to the total weight of avocado used, including the following successive steps:
   (1) Cutting or grinding of avocados, said avocados containing a peel content of 5 to 50% w/w,
   (2) Drying at a temperature between 60 and 150° C., until a residual moisture content less than or equal to 5% is obtained,
   (3) Addition of water to the dried avocados by adding 1 to 5% water or water vapor relative to the weight of dried avocados,
   (4) Oil extraction by mechanical pressure, and then
   (5) Alternatively:
      a. Heat treatment of the extracted oil at a temperature between 80 and 150° C., and then concentration of the oil in its unsaponifiable fraction, or
      b. Concentration of the oil in its unsaponifiable fraction, and then heat treatment at a temperature between 80 and 150° C.,
   (6) followed by saponification and extraction of the unsaponifiable,
   (7) and optionally at least a purification and/or fractionation step,
wherein the avocado unsaponifiable contains at least 0.2% saturated aliphatic hydrocarbons by weight and at least 1% sterols by weight, relative to the total weight of the unsaponifiable.

2. The process for obtaining avocado unsaponifiable enriched in saturated aliphatic hydrocarbons and in sterols according to claim 1, wherein the avocado peels account for 10 to 40% by weight relative to the total weight of avocado used.

3. Avocado unsaponifiable enriched in saturated aliphatic hydrocarbons and in sterols, obtainable by the process according to claim 1, wherein said unsaponifiable comprises at least 0.2% saturated aliphatic hydrocarbons by weight, relative to the total weight of the unsaponifiable.

4. The avocado unsaponifiable enriched in saturated aliphatic hydrocarbons and in sterols according to claim 3, wherein the saturated aliphatic hydrocarbons are linear unbranched hydrocarbons.

5. The avocado unsaponifiable enriched in saturated aliphatic hydrocarbons and in sterols according to claim 3, wherein said unsaponifiable comprises at least 1% sterols by weight, relative to the total weight of the unsaponifiable.

6. The avocado unsaponifiable enriched in saturated aliphatic hydrocarbons and in sterols according to claim 5, wherein the sterols are one or more selected from the group comprised of β-sitosterol, campesterol, stigmasterol, Δ5-avenasterol, Δ7-stigmasterol, citrostadienol, and mixtures thereof.

7. The avocado unsaponifiable enriched in saturated aliphatic hydrocarbons and in sterols according to claim 3, comprising one or more alkyl polyols and/or alkyl furans.

8. Method for preventing and/or treating conjunctive tissue disorders, an articular pathologies and/or periodontal diseases comprising an effective amount of an avocado unsaponifiable enriched in saturated aliphatic hydrocarbons and in sterols of claim 3.

9. The process according to claim 1, wherein the drying (2) is carried out at a temperature between 80 and 120° C.

10. The process according to claim 1, wherein the oil extraction step (4) is carried out at a temperature between 80 and 100° C.

* * * * *